United States Patent
Cantrell

(10) Patent No.: US 10,213,332 B1
(45) Date of Patent: Feb. 26, 2019

(54) SUPRAPUBIC REGION COMPRESSION ASSEMBLY AND METHOD

(71) Applicant: David Wayne Cantrell, Trinity, AL (US)

(72) Inventor: David Wayne Cantrell, Trinity, AL (US)

(*) Notice: Subject to any disclaimer, the term of this patent is extended or adjusted under 35 U.S.C. 154(b) by 218 days.

(21) Appl. No.: 15/080,659

(22) Filed: Mar. 25, 2016

Related U.S. Application Data

(60) Provisional application No. 62/138,096, filed on Mar. 25, 2015, provisional application No. 62/164,097, filed on May 20, 2015.

(51) Int. Cl.
*A61F 5/41* (2006.01)
*A61F 5/00* (2006.01)

(52) U.S. Cl.
CPC .............. *A61F 5/41* (2013.01); *A61F 5/0009* (2013.01); *A61F 2005/414* (2013.01)

(58) Field of Classification Search
CPC ........... A61F 5/41; A61H 19/00; A61H 19/30; A61H 19/34
USPC ...................................... 600/38–41
See application file for complete search history.

(56) References Cited

U.S. PATENT DOCUMENTS

| | | | |
|---|---|---|---|
| 4,203,432 A * | 5/1980 | Koch | A61F 5/41 600/41 |
| 4,440,183 A | 4/1984 | Miller | |
| 4,488,541 A * | 12/1984 | Garcia | A61H 19/34 128/845 |
| 4,724,829 A * | 2/1988 | Knapps | A61F 5/41 600/41 |
| 5,728,043 A * | 3/1998 | Yong | A61F 5/41 600/39 |
| 6,139,515 A | 10/2000 | Ito | |
| D480,145 S | 9/2003 | Slautterback | |
| 7,341,553 B2 | 3/2008 | Egretier | |
| 8,109,569 B2 * | 2/2012 | Mitchell | B60R 11/0235 297/217.1 |
| 8,360,957 B2 | 1/2013 | Kuri | |
| 8,974,369 B2 | 3/2015 | Tomlinson, Jr. | |

FOREIGN PATENT DOCUMENTS

| | | |
|---|---|---|
| CA | 2100370 | 1/1994 |
| CA | 2503233 A1 | 7/2006 |
| CN | 2751792 Y | 1/2006 |
| DE | 202015002335 U1 | 6/2015 |

OTHER PUBLICATIONS

Oxford living dictionary, definition of bar, printed from https://en.oxforddictionaries.com/definition/bar, Jun. 24, 2018.*

* cited by examiner

*Primary Examiner* — Samuel Gilbert
(74) *Attorney, Agent, or Firm* — Bryan Cave Leighton Paisner LLP

(57) ABSTRACT

A suprapubic region compression assembly and method are disclosed for applying pressure to a user's suprapubic region thereby increasing the measurable, visible, or usable length of the user's penis. The suprapubic region compression assembly includes a compression plate, a notch, and a belt. The suprapubic region compression assembly has many advantageous features which provide performance, cost, comfort, and other features desired by consumers to increase the measurable, visible, or usable length of the penis.

20 Claims, 11 Drawing Sheets

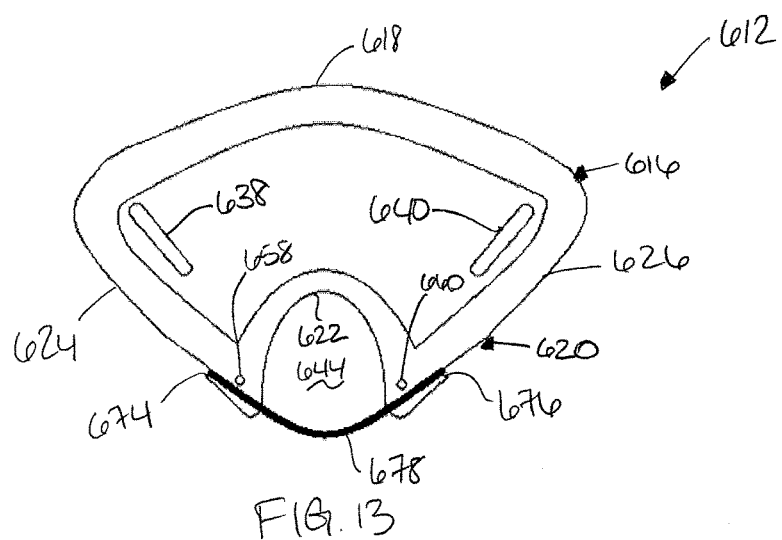
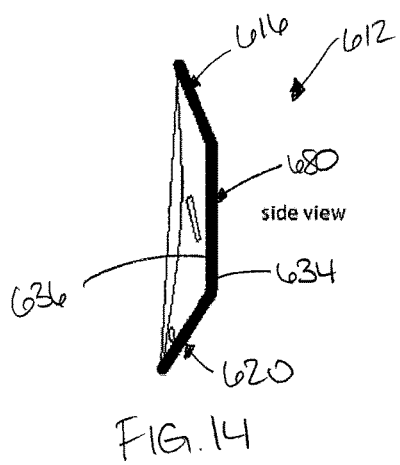
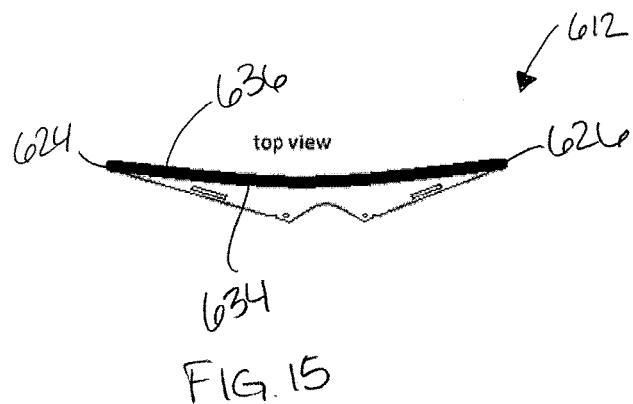
FIG. 13
FIG. 14
FIG. 15

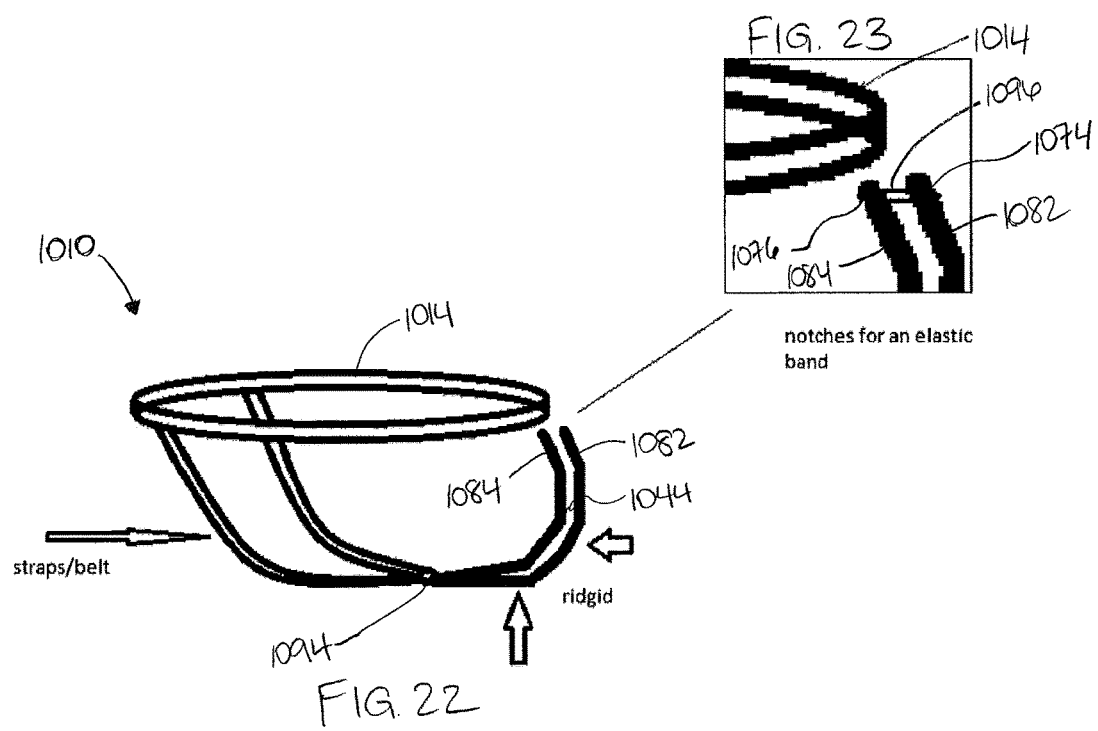

SUPRAPUBIC REGION COMPRESSION ASSEMBLY AND METHOD

CROSS-REFERENCE TO RELATED APPLICATIONS

This application claims priority to U.S. Provisional Patent Application No. 62/138,096, filed Mar. 25, 2015, and U.S. Provisional Patent Application No. 62/164,097, filed May 20, 2015, each of which is incorporated herein by reference in its entirety.

BACKGROUND

The length of a man's penis is important for the pleasure of both partners during sex and for the man's confidence and self-image. Aging and/or weight gain can cause an increase in volume or size of the fatty tissue in the pelvic hypogastric or suprapubic region, directly above the penis. This increase in fatty tissue causes a resulting decrease in the measurable, visible, or usable length of the penis extending from the suprapubic region. To permanently increase the measurable, visible, or usable length of the penis, some men undergo suprapubic region fat pad reduction surgery, which can be costly, painful, and requires recovery time. Accordingly, there is a need for a non-surgical, temporary assembly and method to address challenges presented by pelvic hypogastric or suprapubic region fatty tissue and having the performance, cost, comfort, and other features desired by consumers.

SUMMARY

In one aspect, it is an object of the present invention to provide a suprapubic region compression assembly for compressing the suprapubic region of a user, the assembly comprising: a compression plate having opposite inner and outer surfaces and opposite left and right side edge margins, the compression plate defining a notch positioned between the left and right side edge margins, the notch configured to receive a penis of the user; a belt configured to urge the compression plate toward the user such that the compression plate engages the suprapubic region of the user to apply pressure to the suprapubic region thereby increasing the measurable, visible, or usable length of the penis.

In another aspect, it is an object of the present invention to provide a method of compressing a suprapubic region of a user to increase the measurable, visible, or usable length of the user's penis, the method comprising: attaching a belt around a waist of the user such that an inner surface of a rigid compression plate secured to the belt engages the suprapubic region of the user; positioning the penis of the user adjacent a notch of the compression plate; tightening the belt to force the compression plate against the suprapubic region of the user, thereby compressing the suprapubic region to increase the measurable, visible, or usable length of the penis.

In another aspect, it is an object of the present invention to provide a suprapubic region compression assembly for compressing the suprapubic region of a user, the assembly comprising: a belt configured to be worn by a user; a strap attached to a rear portion of the belt and configured to extend from the belt over a buttock of the user and between legs of the user; a rigid bar attached to the strap at a junction at one end thereof, the rigid bar being configured to engage the suprapubic region of the user to apply pressure to the suprapubic region thereby increasing the measurable, visible, or usable length of the user's penis.

Other objects and features will be in part apparent and in part pointed out hereinafter.

BRIEF DESCRIPTION OF THE DRAWINGS

FIG. 13 is a front elevation of a compression plate according to another embodiment, illustrating a constriction band attached thereto;

FIG. 14 is a side elevation of the compression plate of FIG. 13;

FIG. 15 is a top plan of the compression plate of FIG. 13;

FIG. 22 is a perspective of a suprapubic region compression assembly according to another embodiment; and FIG. 23 is an enlarged, partial view of FIG. 22.

Like reference numerals indicate corresponding parts throughout the drawings.

DETAILED DESCRIPTION

Figure 1:
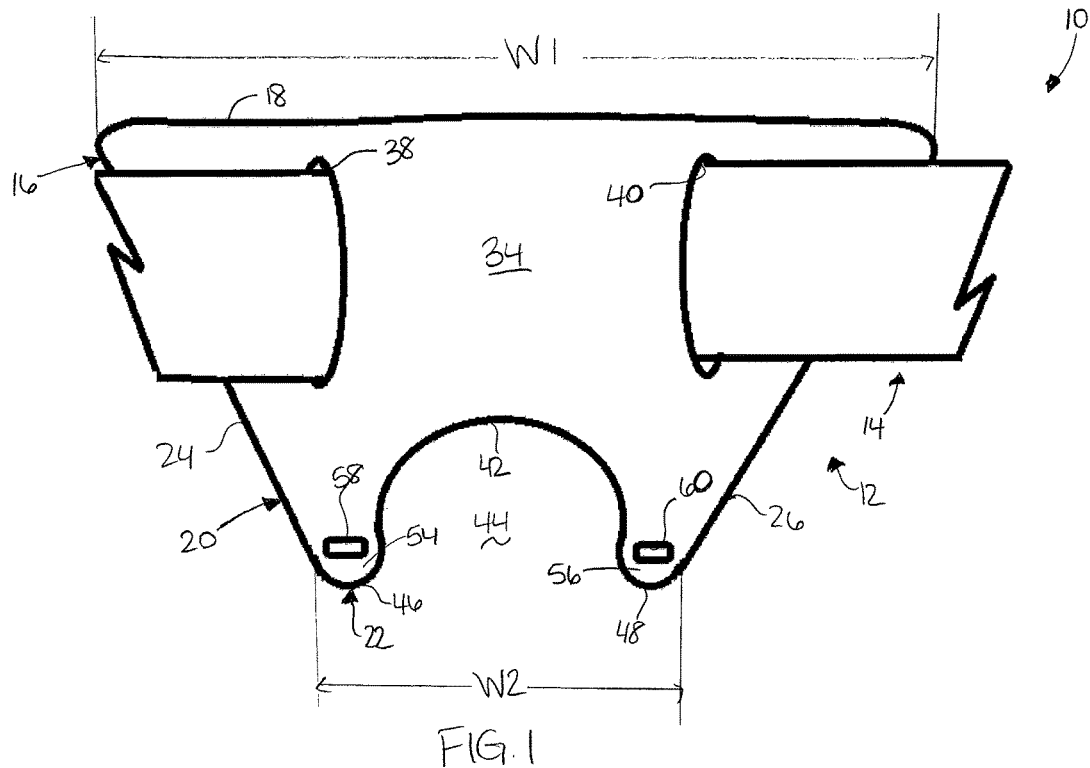
FIG. 1 is a front elevation of a suprapubic region compression assembly according to a first embodiment, including a compression plate and a belt.
Figure 2:
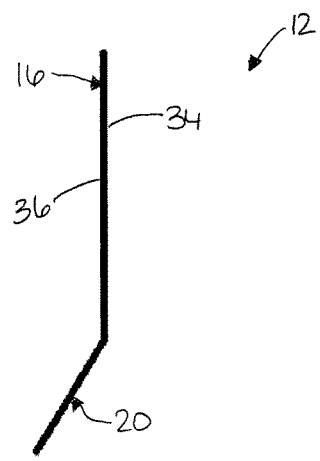
FIG. 2 is a side elevation of the compression plate of FIG. 1.

Referring to FIGS. 1 and 2, a first embodiment of a suprapubic region compression assembly for compressing the suprapubic region of a user is indicated generally at 10. The suprapubic region compression assembly 10 includes a compression plate 12 and a belt or harness 14. The suprapubic region compression assembly 10 is configured to be removably attached to a user such that the compression plate 12 engages the suprapubic region of the user for compression thereof. The compression plate 12 is preferably rigid or semi-rigid such that the compression plate is configured to exert pressure on the suprapubic region to compress the suprapubic region. In one embodiment, the compression plate 12 is rigid. For example, the compression plate 12 may be made of a rigid plastic, metal, or other suitable material. The compression plate 12 may alternatively be made of a semi-rigid plastic, rubber, or other suitable material. In one embodiment, the compression plate 12 is made of a rigid to semi-rigid, durable, injection molded or otherwise moldable medical grade polymer.

Referring still to FIGS. 1 and 2, the compression plate 12 has an upper portion 16 including an upper edge margin 18 and a lower portion 18 adjacent the upper portion and including a lower edge margin 22. The lower portion 20 is contiguous with the upper portion 16. As illustrated, the compression plate 12 is a one-piece, unitary construction, although other configurations are within the scope of the present invention (see, e.g., FIGS. 18-21). In this embodiment, the upper edge margin 18 is generally linear, and the lower edge margin 22 is generally curvilinear, although other configurations are within the scope of the present invention. The orientation of the compression plate 12 in the drawings provides the point of reference for the terms defining relative locations and positions of structures and components of the compression plate, including but not limited to the terms "upper," "lower," "left," and "right," as used throughout the present disclosure.

Opposite left and right side edge margins 24, 26 extend from the upper edge margin 18 to the lower edge margin 22. The compression plate 12 is generally tapered toward the lower edge margin 22. The left and right side edge margins 24, 26 are angled toward each other. As seen in FIG. 1, the compression plate 12 has a first width W1 at the upper edge margin 18 and a second width W2 at the lower edge margin 22. The width W1 is preferably larger than the width W2. The tapering of the compression plate 12 permits the plate to generally conform to the user's anatomy (e.g., going inward at the groin). In addition, and not illustrated in FIGS. 1 and 2, some or all of the compression plate 12 may be curved, formed, or otherwise shaped to also generally conform to the user's anatomy while compressing the suprapubic region (see, e.g., FIGS. 6, 10, 14-15, 17, 19).

The compression plate 12 includes an outer surface 34 and an inner or engaging surface 36. The outer surface 34 faces away from the user during use of the suprapubic region compression assembly 10. The inner surface 36 faces toward the user during use of the suprapubic region compression assembly 10 and engages the suprapubic region of the user. As shown in FIG. 2, the lower portion 20 of the compression plate 12 is angled relative to the upper portion 16. The lower portion 20 is angled toward the inner surface 36, i.e., away from the outer surface 34. Alternatively, the lower portion 20 may be curved toward the inner surface 36, i.e., away from the outer surface 34. It is understood that the lower portion 20 may not be angled or curved relative to the upper portion 16 (i.e., the upper and lower portions can be coplanar) within the scope of the present invention.

The compression plate 12 includes first and second belt mounting slots 38, 40. As illustrated in FIG. 1, the belt mounting slots 38, 40 are in the upper portion 16 of the compression plate 12, although other configurations are within the scope of the present invention. The belt mounting slots 38, 40 are configured to receive the belt 14. The belt 14 is received in and extends through both the first and second belt mounting slots 38, 40 to securely attach the compression plate 12 to the belt. Alternatively, the belt 14 may be secured to or removably connected to the compression plate 12 using adhesive, hook-and-loop fasteners, molding, or one or more clips, buckles, buttons, clasps, or any other suitable attachment. The belt 14 is preferably an adjustable belt that can be adjusted in length to accommodate different sized users. The belt 14 may be any type of adjustable belt, such as a single belt that can be doubled upon and secured to itself, or two belts with a joining clasp, buckle, or other fastener, or any other suitable adjustable belt. Adjustable, belt 14 can be an elastic belt that stretches to accommodate different sized users. The belt 14 is configured to wrap around the waist or hips of a user to secure the compression plate 12 to the user.

Referring to FIG. 1, a central portion 42 of the generally curvilinear lower edge margin 22 of the compression plate 12 extends upward toward the upper edge margin 18 to define a notch or opening 44 having an entrance facing away from the upper portion 16 of the plate 12. The notch 44 is positioned between the left and right side edge margins 24, 26 and is configured to receive the user's penis. Optionally, the lower edge margin 22 may engage the penis when the compression plate 12 is in place engaging the suprapubic region of the user. Outer portions 46, 48 of the lower edge margin 22 extend from the respective left and right side edge margins 24, 26 to the central portion 42 and define first and second tabs 54, 56. Each tab 54, 56 includes an ancillary strap slot 58, 60. The ancillary strap slots 58, 60 are configured to receive ancillary straps (see, e.g., FIGS. 3 and 4). It is understood that the ancillary strap slots 58, 60 (and corresponding ancillary straps) may be omitted within the scope of the present invention.

Figure 3:
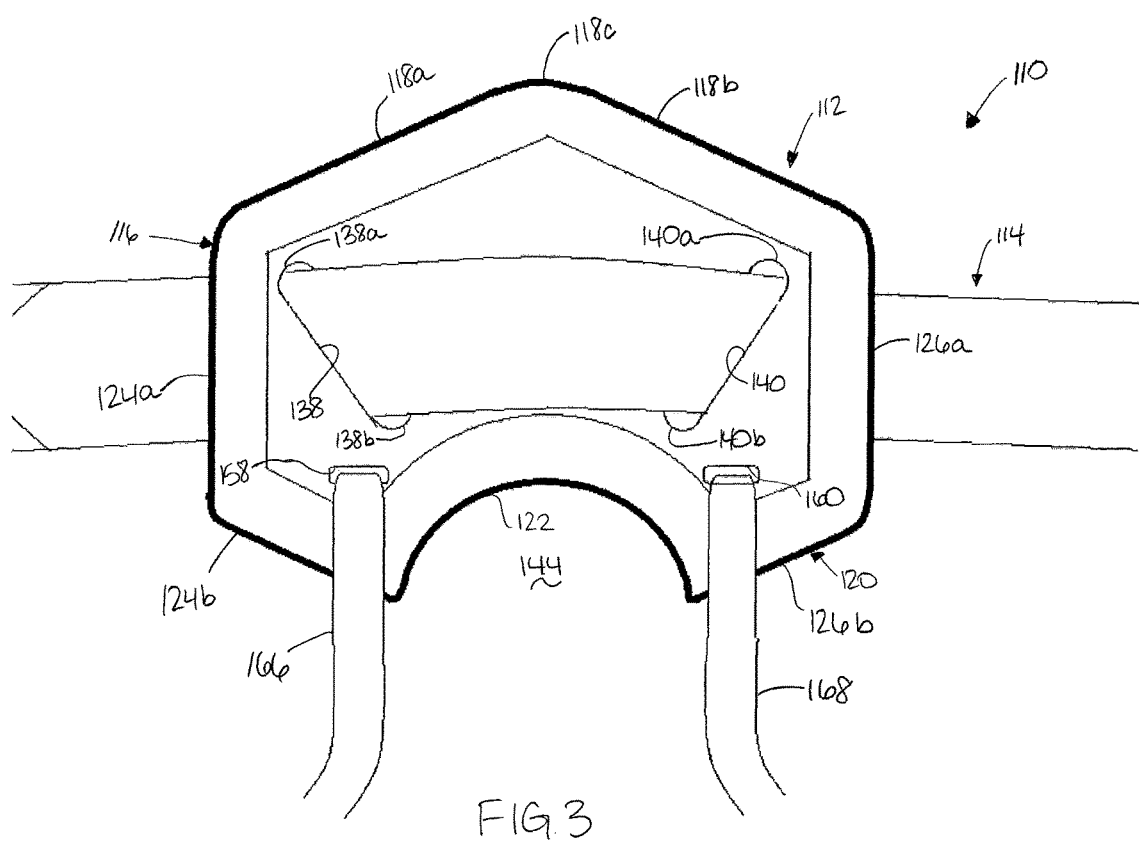
FIG. 3 is a front elevation of a suprapubic region compression assembly according to another embodiment, including a compression plate, a belt, and ancillary straps.
Figure 4:
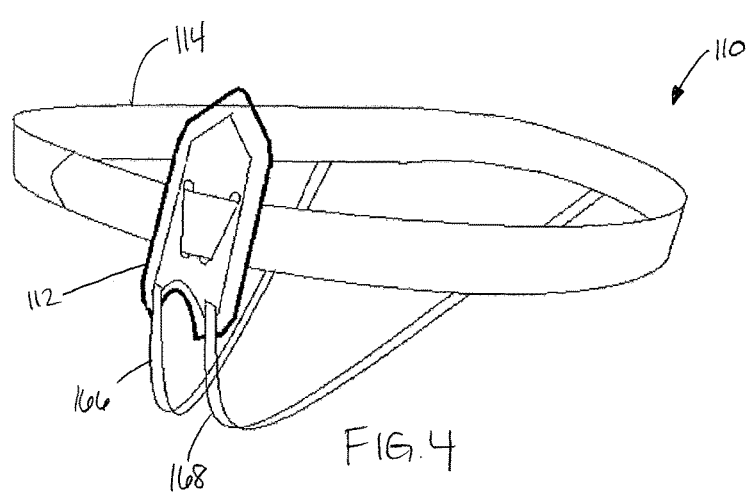
FIG. 4 is a perspective of the suprapubic region compression assembly of FIG. 3.

Referring now to FIGS. 3 and 4, a second embodiment of a suprapubic region compression assembly for compressing the suprapubic region of a user is indicated generally at 110. The suprapubic region compression assembly 110 is substantially similar to the suprapubic region compression assembly 10 described above, with differences as pointed out herein.

The suprapubic region compression assembly 110 includes a compression plate 112 and a belt or harness 114. The belt 114 is an adjustable belt as described above with reference to belt 14. As described above with reference to compression plate 12, the compression plate 112 is preferably rigid or semi-rigid such that the compression plate is configured to exert pressure on the suprapubic region to compress the suprapubic region. The compression plate 112 includes an upper portion 116 and a lower portion 120. As described above with reference to compression plate 12, the lower portion 120 may extend inward (i.e., away from the outer surface 134) relative to the upper portion 116, although it is not necessary within the scope of the present invention.

In this embodiment, the compression plate 112 is generally hexagonal in shape. The upper edge margin 118 includes first and second upper edge margin portions 118a and 118b converging at an apex 118c. The left and right side edge margins, 124, 126 each include a first vertical portion 124a, 126a and a second angled portion 124b, 126b extending toward the opposite side edge margin at an angle relative to the respective first vertical portion. The compression plate 112 tapers toward the lower edge margin 122 to conform to the user's anatomy (e.g., going inward at the groin). The lower edge margin 122 is generally curvilinear (e.g., generally semi-circular) and extends upward toward the upper edge margin 118 to define a notch or opening 44 having an entrance facing away from the upper portion 116 of the plate 112.

Referring still to FIGS. 3 and 4, the compression plate 112 includes first and second belt mounting slots 138, 140 configured to receive the belt 114 as described above with reference to compression plate 12. In this embodiment, the belt mounting slots 138, 140 are angled toward each other. Upper ends 138a, 140a of the slots 138, 140 are farther from each other than lower ends 138b, 140b of the slots. Angling the belt mounting slots 138, 140 focuses pressure downward to maximize the compression of the suprapubic region adjacent the penis.

The compression plate 112 includes ancillary strap slots 158, 160. The ancillary strap slots 158, 160 are configured to receive ancillary straps 166, 168. Each ancillary strap 166, 168 is received in and extends through the corresponding ancillary strap slot 158, 160. Each ancillary strap 166, 168 is attached to both the compression plate 112 and the belt 114. The ancillary straps 166, 168 may be adjustable or may have a fixed length. In one embodiment, the ancillary straps may be elastic straps that stretch to accommodate different sized users. The ancillary straps may be removably attached to the compression plate 112 and/or the belt 114. A user may attach the ancillary straps 166, 168 after the belt 114 is in place by extending each strap between the legs, along the groin, and around the buttocks to attach to the compression plate 112 and/or the belt 114. Alternatively, the user may attach the ancillary straps 166, 168 to the compression plate 112 and/or the belt 114 prior to donning the suprapubic region compression assembly 110, and then step into the assembly like a brief style garment. Alternatively, the ancillary straps may be fixedly attached to both the compression plate 112 and the belt 114, in which case the user would step into the assembly like a brief-style garment. The use of two ancillary straps provides comfort and stability that a single strap, similar to that of a thong-style garment, does not. The ancillary straps 166, 168 pull the lower portion 120 of the compression plate 112 inward toward the user to maximize compression of the suprapubic region. It is understood that the ancillary strap slots 158, 160 and the ancillary straps 166, 168 may be omitted within the scope of the present invention.

Figure 5:
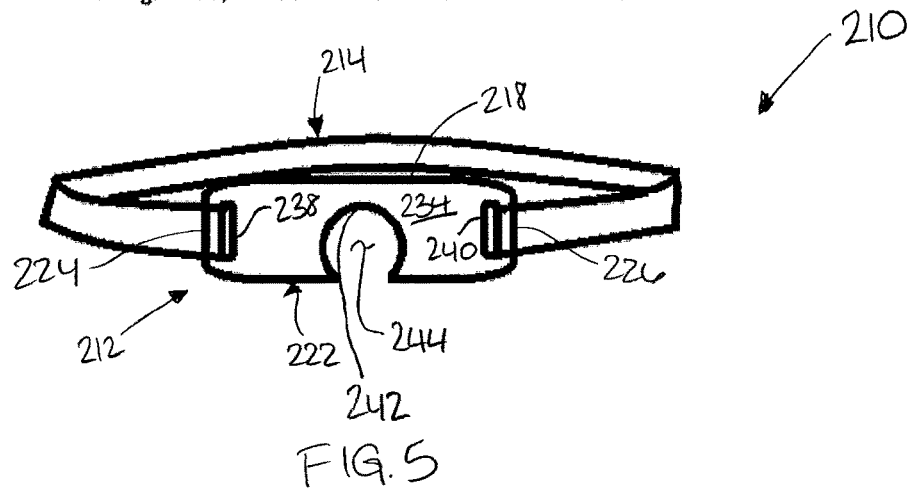
FIG. 5 is a perspective of a suprapubic region compression assembly according to another embodiment, including a compression plate and a belt.
Figure 6:
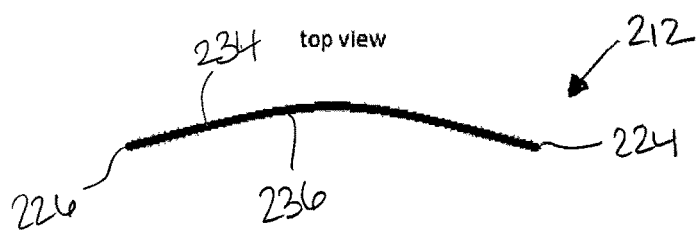
FIG. 6 is a top plan of the compression plate of FIG. 5.

Referring now to FIGS. 5 and 6, a third embodiment of a suprapubic region compression assembly for compressing the suprapubic region of a user is indicated generally at 210. The suprapubic region compression assembly 210 is substantially similar to the compression plate assemblies 10, 110 described above, with differences as pointed out herein.

The suprapubic region compression assembly 210 includes a compression plate 212 and a belt or harness 214. The belt 214 is an adjustable belt as described above with reference to belt 14. The compression plate 212 is preferably rigid or semi-rigid, as described above with reference to compression plate 12. In this embodiment, the compression plate 212 is generally rectangular in shape. The lower edge margin 222, particularly a central portion 242 of the lower edge margin, extends upward toward the upper edge margin 218 to define a notch or opening 244 having an entrance facing away from the upper edge margin of the plate 212. The compression plate 212 includes first and second belt mounting slots 238, 240 adjacent the respective left and right side edge margins 224, 226. As illustrated in FIG. 6, the compression plate 212 is generally curved such that the left and right side edge margins 224, 226 extend inward toward the user so that the inner surface 236 generally conforms to the user's anatomy.

Figure 7:
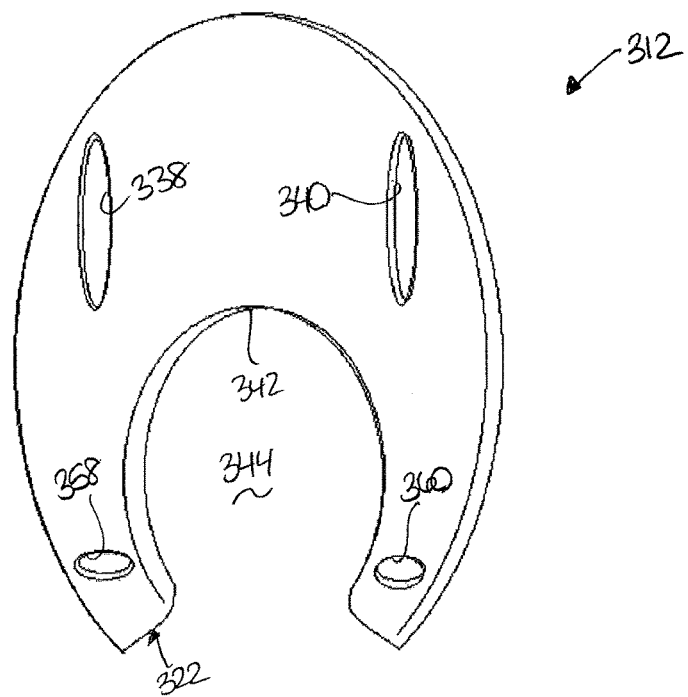
FIG. 7 is a front perspective of a compression plate according to another embodiment.
Figure 8:
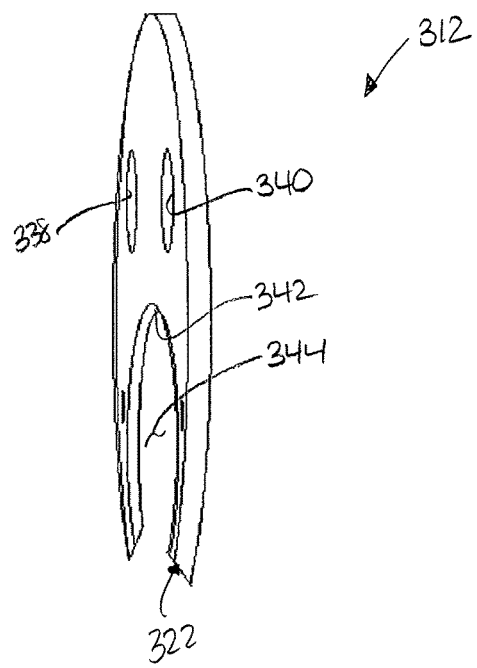
FIG. 8 is a side perspective of the compression plate of FIG. 7.

Referring now to FIGS. 7 and 8, another embodiment of a compression plate for compressing the suprapubic region of a user is indicated generally at 312. The compression plate 312 is substantially similar to the compression plates 12, 112, 212 described above, with differences as pointed out herein.

As described above with reference to compression plate 12, the compression plate 312 is preferably rigid or semi-rigid such that the compression plate is configured to exert pressure on the suprapubic region to compress the suprapubic region. In this embodiment, the compression plate 312 has a generally oval shape. The compression plate 312 generally tapers toward the lower edge margin 322 to conform to the user's anatomy. A central portion 342 of the lower edge margin 322 extends upward to define a notch or opening 344 having an entrance facing downward. The compression plate 312 includes belt mounting slots 338, 340 and ancillary strap slots 358, 360, as described above with reference to compression plates 12, 112, 212. In this embodiment, the compression plate 312 is planar.

Figure 9:
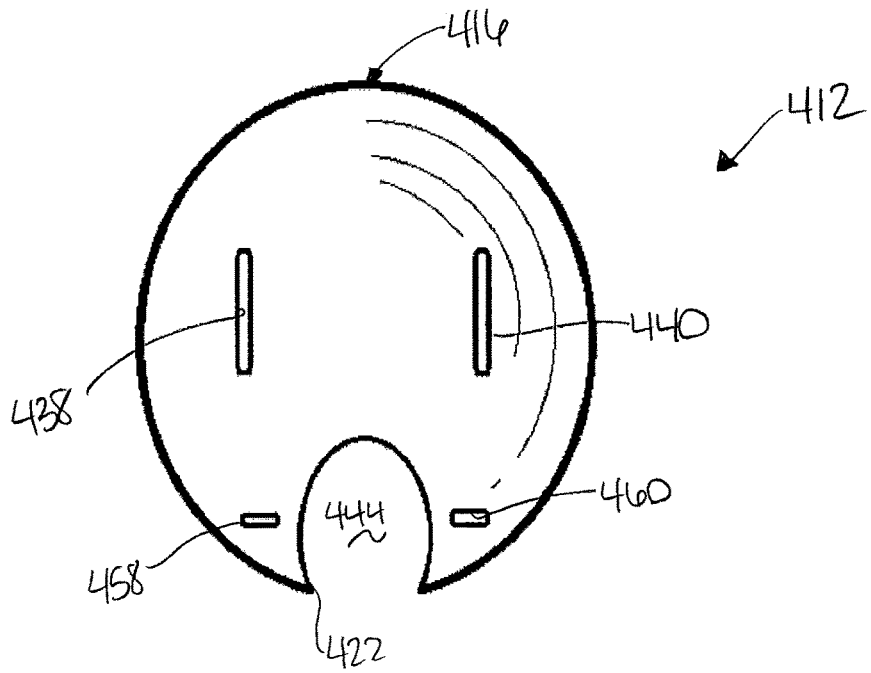
FIG. 9 is a front elevation of a compression plate according to another embodiment.
Figure 10:
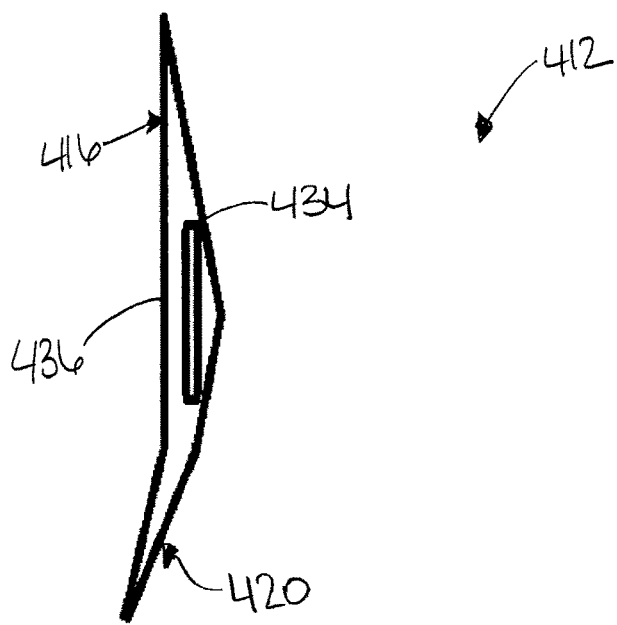
FIG. 10 is a side elevation of the compression plate of FIG. 9.

Referring now to FIGS. 9 and 10, another embodiment of a compression plate for compressing the suprapubic region of a user is indicated generally at 412. The compression plate 412 is substantially similar to the compression plates 12, 112, 212, 312 described above, with differences as pointed out herein.

As described above with reference to compression plate 12, the compression plate 412 is preferably rigid or semi-rigid such that the compression plate is configured to exert pressure on the suprapubic region to compress the suprapubic region. In this embodiment, the compression plate 412 has a generally oval shape. The compression plate 412 generally tapers toward the lower edge margin 422 to conform to the user's anatomy. The lower edge margin 422 extends upward toward the upper portion 416 to define a notch or opening 444 having an entrance facing away from the upper portion of the plate 412. The compression plate 412 includes belt mounting slots 438, 440 and ancillary strap slots 458, 460, as described above with reference to compression plates 12, 112, 212, 312. As shown in FIG. 10, the lower portion 420 of the compression plate 412 is angled or curved relative to the upper portion 416. The lower portion 420 is angled or curved toward the inner surface 436, i.e., away from the outer surface 434.

Figure 11:
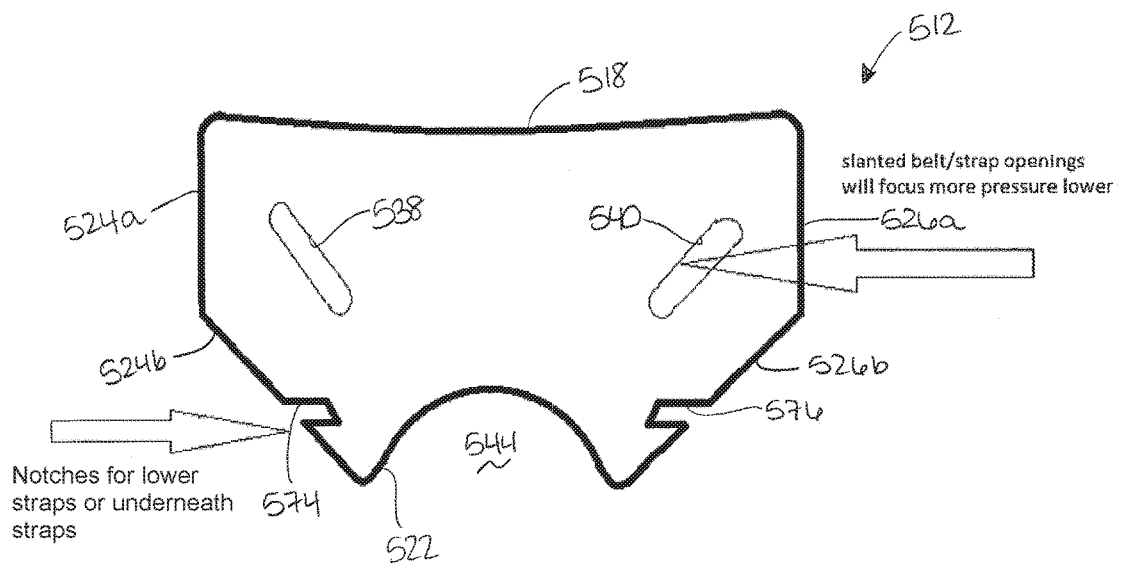
FIG. 11 is a front elevation of a compression plate according to another embodiment.
Figure 12:
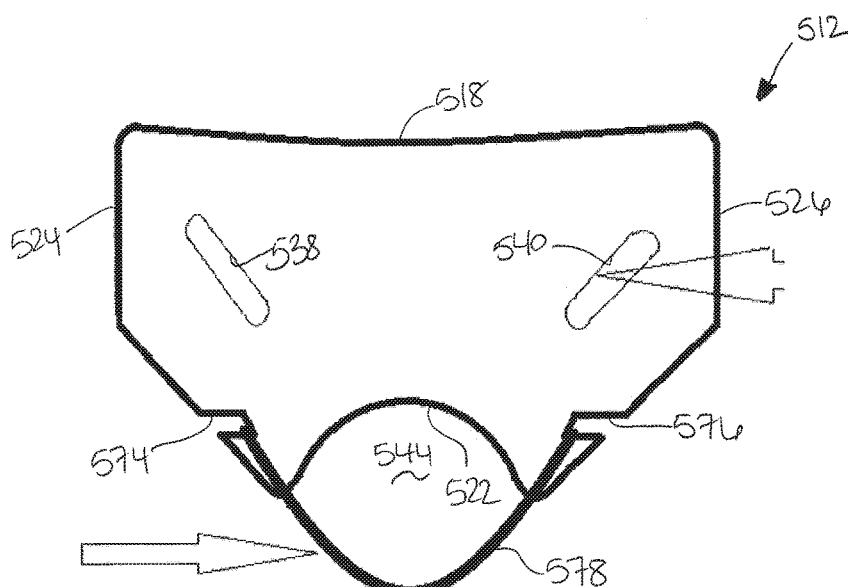
FIG. 12 is a front elevation of the compression plate of FIG. 11, illustrating a constriction band attached thereto.

Referring now to FIGS. 11 and 12, another embodiment of a compression plate for compressing the suprapubic region of a user is indicated generally at 512. The compression plate 512 is substantially similar to the compression plates 12, 112, 212, 312, 412 described above, with differences as pointed out herein.

As described above with reference to compression plate 12, the compression plate 512 is preferably rigid or semi-rigid such that the compression plate is configured to exert pressure on the suprapubic region to compress the suprapubic region. The compression plate 512 generally tapers toward the lower edge margin 522 to conform to the user's anatomy. The lower edge margin 522 extends upward toward the upper edge margin 518 to define a notch or opening 544 having an entrance facing away from the upper edge margin of the plate 512. The compression plate 512 includes belt mounting slots 538, 540 as described above with reference to compression plates 12, 112, 212, 312, 412. As illustrated, the belt mounting slots 538, 540 are angled to focus pressure downward, as described above with reference to compression plate 112.

The left and right side edge margins 524, 526 each include a first vertical portion 524a, 526a and a second angled portion 524b, 526b extending toward the opposite side edge margin at an angle relative to the respective first vertical portion. Each angled portion 524b, 526b includes an indent 574, 576. The angled portion 524b of the left side edge margin 524 includes an indent 574 extending inward toward the right edge margin 526 and having an entrance facing away from the right edge margin. The angled portion 526b of the right side edge margin 526 includes an indent 576 extending inward toward the left edge margin 524 and having an entrance facing away from the left edge margin. The indents 574, 576 are configured to receive a constriction strap or band 578 (FIG. 12). The constriction band 578 can be an elastic band or other suitable band having a fixed or adjustable length. The constriction band 578 is configured to be received in both indents 574, 576 to maintain the constriction band 578 in place relative to the compression plate 512. In use, the constriction band is configured and positioned to apply pressure circumferentially or semi-circumferentially, for example in conjunction with the radius of the notch in the plate, to the base of the penis or at least a portion of the base of the penis to maintain an erection. In this embodiment, the compression plate 512 does not include ancillary strap slots. However, it is understood that the compression plate 512 can include ancillary strap slots (and corresponding ancillary straps) in addition to the indents (and corresponding constriction band).

Referring now to FIGS. 13-15, another embodiment of a compression plate for compressing the suprapubic region of a user is indicated generally at 612. The compression plate 612 is substantially similar to the compression plates 12, 112, 212, 312, 412, 512 described above, with differences as pointed out herein.

As described above with reference to compression plate 12, the compression plate 612 is preferably rigid or semi-rigid such that the compression plate is configured to exert pressure on the suprapubic region to compress the suprapubic region. The compression plate 612 generally tapers toward the lower edge margin 622 to conform to the user's anatomy. The lower edge margin 622 extends upward toward the upper edge margin 618 to define a notch or opening 644 having an entrance facing away from the upper portion 616 of the plate 612. The compression plate 612 includes belt mounting slots 638, 640 and ancillary strap slots 658, 660 as described above with reference to compression plates 12, 112, 212, 312, 412, 512. As illustrated, the belt mounting slots 638, 640 are angled to focus pressure downward, as described above with reference to compression plate 112. The left and right side edge margins 624, 626 include indents 674, 676 positioned in the lower portion 620 of the plate 612. The indents 674, 676 receive a constriction band 678, as described above with reference to plate 512.

As shown in FIG. 14, the upper and lower portions 616, 620 of the compression plate 612 are angled or curved relative to a central portion 680 of the plate. The upper and lower portions 616, 620 are angled or curved toward the inner surface 636, i.e., away from the outer surface 634. It is understood that only one of the upper and lower portions may be angled or curved inward within the scope of the present invention. As illustrated in FIG. 15, the compression plate 612 is generally curved such that the left and right side edge margins 624, 626 extend inward toward the user so that the inner surface 634 generally conforms to the user's anatomy.

Figure 16:
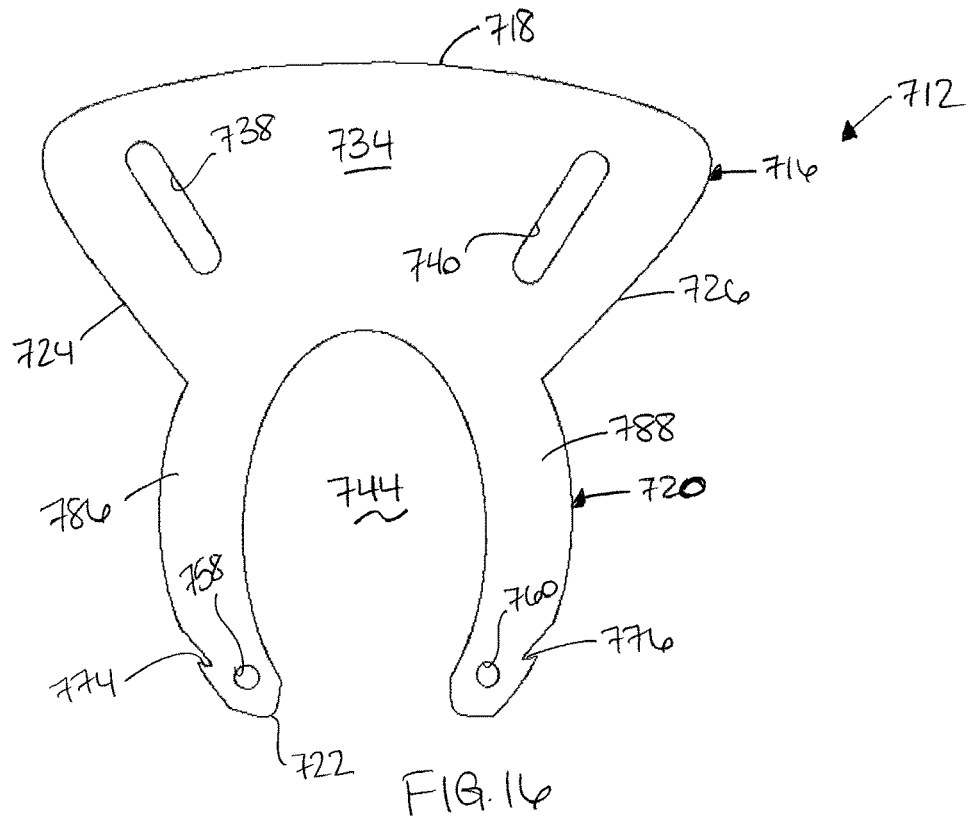
FIG. 16 is a front elevation of a compression plate according to another embodiment.
Figure 17:
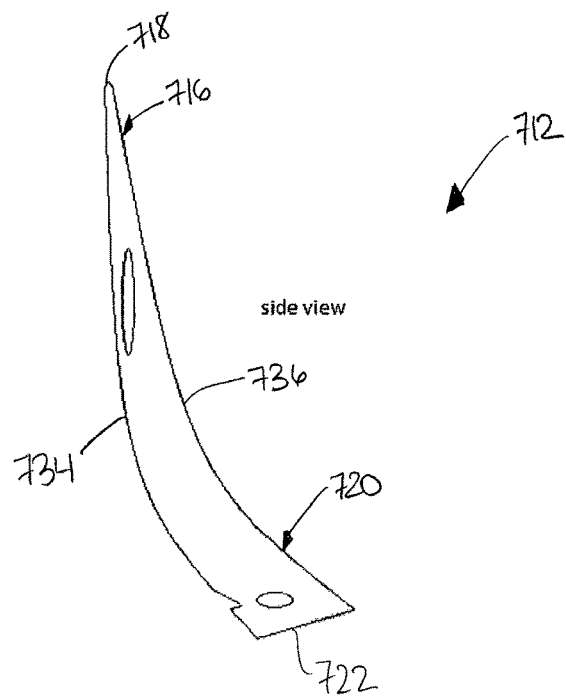
FIG. 17 is a side elevation of the compression plate of FIG. 16.

Referring now to FIGS. 16 and 17, another embodiment of a compression plate for compressing the suprapubic region of a user is indicated generally at 712. The compression plate 712 is substantially similar to the compression plates 12, 112, 212, 312, 412, 512, 612 described above, with differences as pointed out herein.

As described above with reference to compression plate 12, the compression plate 712 is preferably rigid or semi-rigid such that the compression plate is configured to exert pressure on the suprapubic region to compress the suprapubic region. The compression plate 712 generally tapers toward the lower edge margin 722 to conform to the user's anatomy. The lower edge margin 722 extends upward toward the upper edge margin 718 to define a notch or opening 744 having an entrance facing away from the upper portion 716 of the plate 712. The compression plate 712 includes belt mounting slots 738, 740 and ancillary strap slots 758, 760 as described above with reference to compression plates 12, 112, 212, 312, 412, 512, 612. As illustrated, the belt mounting slots 738, 740 are angled to focus pressure downward, as described above with reference to compression plate 112. In this embodiment, the lower portion 720 of the plate 712 includes first and second arms 786, 788. The left and right side edge margins 724, 726 are generally linear at the upper portion 716 and generally rounded or curved at the lower portion 720 to define the arms 786, 788 with the lower edge margin 722. The left and right side edge margins 724, 726 include indents 774, 776 positioned in the lower portion 720 of the plate 712. The indents 774, 776 receive a constriction band 778, as described above with reference to plate 512. As illustrated, the ancillary strap slots 758, 760 and the indents 774, 776 are located in the respective arms 786, 788. As shown in FIG. 17, the compression plate 712 is angled or curved inward from the upper portion 716 to the lower portion 720. The compression plate is angled or curved toward the inner surface 736, i.e., away from the outer surface 734.

Figure 18:
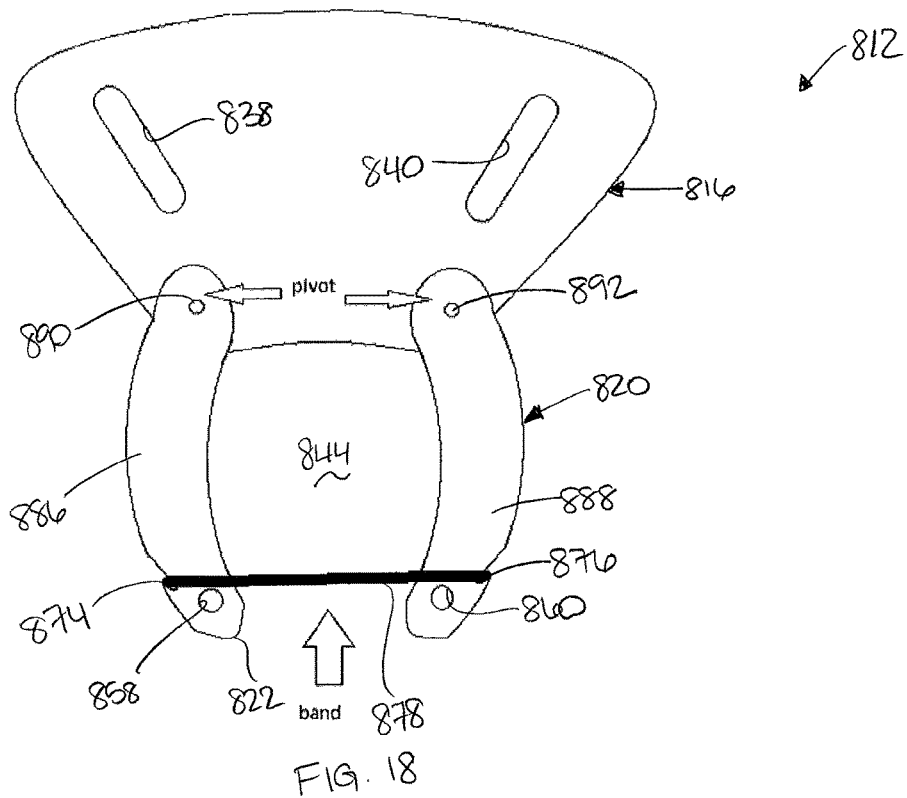
FIG. 18 is a front elevation of a compression plate according to another embodiment, illustrating a constriction band attached thereto.
Figure 19:
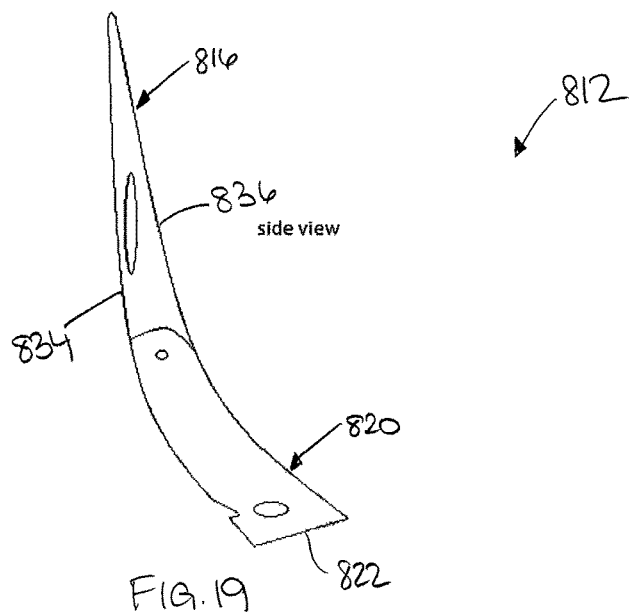
FIG. 19 is a side elevation of the compression plate of FIG. 18.

Referring now to FIGS. 18 and 19, another embodiment of a compression plate for compressing the suprapubic region of a user is indicated generally at 812. The compression plate 812 is substantially similar to the compression plates 12, 112, 212, 312, 412, 512, 612, 712 described above, with differences as pointed out herein.

As described above with reference to compression plate 12, the compression plate 812 is preferably rigid or semi-rigid such that the compression plate is configured to exert pressure on the suprapubic region to compress the suprapubic region. The compression plate 812 generally tapers toward the lower edge margin 822 to conform to the user's anatomy. In this embodiment, the lower portion 820 of the plate 812 comprises arms 886, 888 that are formed separately from the upper portion 816 and are pivotally attached thereto at respective pivot points 890, 892. A notch or opening 844 is defined between the arms 886, 888 and has an entrance facing away from the upper portion 816 of the plate. The size of the notch 844 is adjustable by pivoting the arms 886, 888. Thus, the size of the notch 844 can be increased or decreased to fit a user's penis. The compression plate 812 includes belt mounting slots 838, 840 and ancillary strap slots 858, 860 as described above with reference to compression plates 12, 112, 212, 312, 412, 512, 612, 712. As illustrated, the belt mounting slots 838, 840 are angled to focus pressure downward, as described above with reference to compression plate 112. In this embodiment, the upper portion 816 includes the belt mounting slots 838, 840, and the lower portion 820 (i.e., the arms 886, 888) includes the ancillary strap slots 858, 860. The arms 886, 888 also include indents 874, 876 for receiving a constriction band 878, as described above with reference to plate 512. The constriction band 878 can be used to maintain the relative positioning of the arms 886, 888 (and therefore maintain the size of the notch 844), to apply pressure to the base of the penis to maintain an erection, or both. As shown in FIG. 19, the compression plate 812 is angled or curved inward from the upper portion 816 to the lower portion 820. The compression plate is angled or curved toward the inner surface 836, i.e., away from the outer surface 834.

Figure 20:
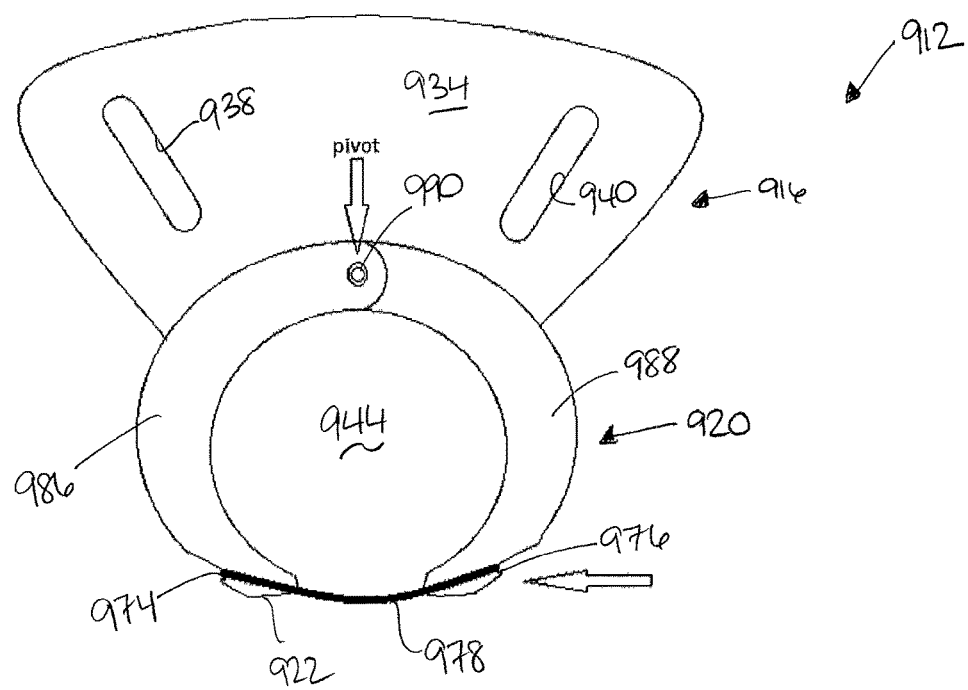
FIG. 20 is a front elevation of a compression plate according to another embodiment, illustrating a constriction band attached thereto.
Figure 21:
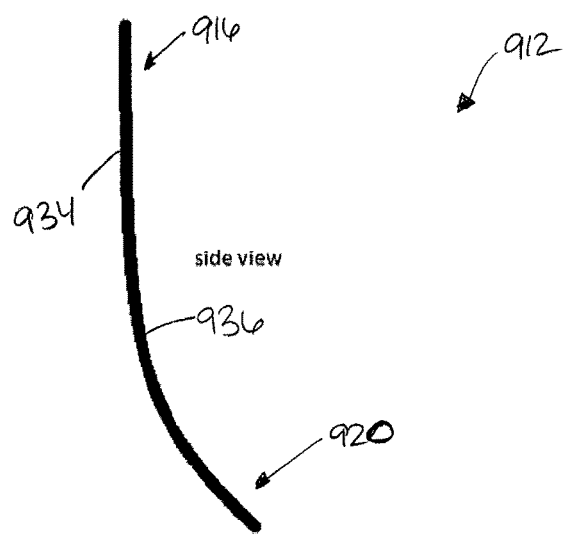
FIG. 21 is a side elevation of the compression plate of FIG. 20.

Referring now to FIGS. 20 and 21, another embodiment of a compression plate for compressing the suprapubic region of a user is indicated generally at 912. The compression plate 912 is substantially similar to the compression plates 12, 112, 212, 312, 412, 512, 612, 712, 812 described above, with differences as pointed out herein.

As described above with reference to compression plate 12, the compression plate 912 is preferably rigid or semi-rigid such that the compression plate is configured to exert pressure on the suprapubic region to compress the suprapubic region. The compression plate 912 generally tapers toward the lower edge margin 922 to conform to the user's anatomy. In this embodiment, the lower portion 920 of the plate 912 comprises arms 986, 988 that are formed separately from the upper portion 916 and are pivotally attached thereto at a single pivot point 990. A notch or opening 944 is defined between the arms 986, 988 and has an entrance facing away from the upper portion 916 of the plate. The size of the notch 944 is adjustable by pivoting the arms 986, 988. Thus, the size of the notch 944 can be increased or decreased to fit a user's penis. The compression plate 912 includes belt mounting slots 938, 940 as described above with reference to compression plates 12, 112, 212, 312, 412, 512, 612, 712, 812. As illustrated, the belt mounting slots 938, 940 are angled to focus pressure downward, as described above with reference to compression plate 112. In this embodiment, the upper portion 916 includes the belt mounting slots 938, 940. The lower portion 920 (i.e., the arms 986, 988) includes indents 974, 976 for receiving a constriction band 978, as described above with reference to plate 512. The constriction band 978 can be used to maintain the relative positioning of the arms 986, 988 (and therefore maintain the size of the notch 944), to apply pressure to the base of the penis to maintain an erection, or both. As shown in FIG. 21, the compression plate 912 is angled or curved inward from the upper portion 916 to the lower portion 920. The compression plate is angled or curved toward the inner surface 936, i.e., away from the outer surface 934.

Referring now to FIGS. 22 and 23, another embodiment of a suprapubic region compression assembly is generally indicated at 1010. The suprapubic region compression assembly 1010 includes first and second rigid bars 1082, 1084, a belt or harness 1014, and first and second ancillary straps 1066, 1068. The belt 1014 is an adjustable belt as described above with reference to belt 14. The ancillary straps 1066, 1068 can be flexible, elastic, semi-rigid, fixed length, adjustable length, deformable, or any other suitable type of strap. The ancillary straps 1066, 1068 are attached to a rear portion of the belt 1014 and during use extend over the buttocks and between the legs along the groin. The bars 1082, 1084 are attached to the ancillary belts 1066, 1068 at junction 1094. The rigid bars 1082, 1084 are configured to engage and exert pressure on the suprapubic region of the user. A notch 1044 is defined between the rigid bars 1082, 1084 and is configured to receive the user's penis. The rigid bars 1082, 1084 are sufficiently rigid to maintain their shape to exert pressure against the suprapubic region. As shown in FIG. 22, the ends of the bars 1082, 1084 are spaced from each other at an upper portion of the assembly 1010, and converge at a lower portion of the assembly. Similarly, the ancillary straps 1066, 1068 are spaced from each other at the attachment to the belt 1014, and converge at a lower portion of the assembly. The two straps 1066, 1068 and the two bars 1082, 1084 come together and are joined at the junction 1094.

Referring to FIG. 23, each bar 1082, 1084 includes an indent 1074, 1076 configured to receive an elastic band 1096. The elastic band 1096 is received in each indent 1074, 1076 and attaches to a protrusion (not shown) on the belt 1014 to secure the bars 1082, 1084 to the belt and thereby compress the suprapubic region of the user. Alternatively, the bars 1082 may be removably connected to the belt or an optional compression plate (not shown) using hook-and-loop fasteners, or one or more clips, buckles, buttons, clasps, or any other suitable attachment. The bars 1082, 1084 can be coated with or embedded in a relatively soft material for the comfort of the user. Also for the comfort of the user, the ancillary straps are made of a material that is more flexible than the bars (i.e., the bars are more rigid than the straps).

In use, the user dons the suprapubic region compression assemblies as described above by wrapping the belt around his waist such that the inner surface of the compression plate or compression bars engages the suprapubic region of the user. The user's penis is positioned in the notch to provide maximum coverage and compression of the suprapubic region. The compression plate may be positioned such that the lower edge margin, or edge defining the notch, engages the penis, although this is not required. The user pulls the belt taut to urge the compression plate against the suprapubic region to compress the suprapubic region. The lower portion of the compression plate angling or curving inward toward the user permits the compression plate to better conform to the user's anatomy, while also ensuring maximum compression of the suprapubic region. The compression plate is a rigid structure that applies pressure to the pubic area above and to the sides of the penis at the base of the penis through force applied by tension from the belt and the optional ancillary straps. The suprapubic region compression assembly thus compresses the suprapubic region to increase the measurable, visible, or usable length of the user's penis. The suprapubic region compression assembly therefore simulates the effects of a suprapubic fat pad reduction surgery without requiring the expense, pain, and recovery time of the surgery.

Optionally, ancillary straps may be received in and extend through ancillary strap slots and attach to a rear portion of the belt. The ancillary straps extend between the user's legs along the groin and up around the buttocks to the belt, similar to a brief style garment. The ancillary straps pull the lower portion of the compression plate inward toward the user to maximize compression of the suprapubic region.

Optionally, a constriction band may be received in indents in the lower portion of the compression plate. The constriction band extends below the penis and applies pressure circumferentially or semi-circumferentially, for example in conjunction with the radius of the notch in the plate, to the base of the penis or at least a portion of the base of the penis to maintain an erection.

The suprapubic region compression assembly can also be used to retain the foreskin or prepuce of the user to expose the user's glans, such as by engaging the slack of the foreskin with the lower edge margin of the compression plate. Engagement may be accomplished by incorporating the optional constriction band with the compression plate, having the effect of holding taut the slack of the foreskin. In a similar manner, the suprapubic region compression assembly incorporating the optional constriction band with the compression plate can be used to retain a condom on the user's penis.

Having described the invention in detail, it will be apparent that modifications and variations are possible without departing from the scope of the invention defined in the appended claims.

When introducing elements of the present invention or the illustrated embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense. It is understood that any feature of any embodiment described above may be combined with any other feature(s) of any other embodiment(s).

What is claimed:

1. A suprapubic region compression assembly for compressing a suprapubic region of a user, the assembly comprising:
   a compression plate having opposite inner and outer surfaces and opposite left and right side edge margins, the compression plate defining a notch positioned between the left and right side edge margins, the notch configured to receive a penis of the user, the compression plate comprising a lower portion including the notch and an upper portion, the lower portion having the notch being curved or angled inward toward the inner surface relative to the upper portion to compress the suprapubic region of the user; and
   a belt configured to urge the compression plate toward the user such that the compression plate engages the suprapubic region of the user to apply pressure to the suprapubic region thereby increasing a measurable, visible, or usable length of the penis.

2. The suprapubic region compression assembly of claim 1, wherein the compression plate is rigid.

3. The suprapubic region compression assembly of claim 2, wherein the compression plate tapers from the upper portion toward the lower portion.

4. The suprapubic region compression assembly of claim 3, wherein the left and right side edge margins extend inward toward each other to conform to the user's anatomy.

5. The suprapubic region compression assembly of claim 2, wherein the left and right side edge margins extend inward toward each other to conform to the user's anatomy.

6. The suprapubic region compression assembly of claim 2, wherein the compression plate defines at least one mounting slot.

7. The suprapubic region compression assembly of claim 6, further comprising at least one ancillary strap, wherein the at least one ancillary strap is configured to be received in a mounting slot to urge a lower portion of the compression plate toward the user to compress the suprapubic region of the user.

8. The suprapubic region compression assembly of claim 1, wherein the left side edge margin includes a first indent and the right side edge margin includes a second indent generally aligned with the first indent, the first and second indents being configured to receive a constriction band for applying pressure to at least a portion of a base of the penis to maintain an erection.

9. The suprapubic region compression assembly of claim 1, wherein the left side edge margin includes a first indent and the right side edge margin includes a second indent generally aligned with the first indent.

10. The suprapubic region compression assembly of claim 9, further comprising a constriction band received in the first and second indents, the constriction band configured to extend below the penis and apply pressure to a base of the penis to maintain an erection.

11. The suprapubic region compression assembly of claim 1, wherein the compression plate comprises an upper portion and a lower portion, the lower portion comprising first and second arms pivotally attached to the upper portion, the arms defining the notch such that a size of the notch is adjustable upon movement of the arms relative to each other.

12. The suprapubic region compression assembly of claim 11, wherein each of the first and second arms is pivotally attached to the upper portion at a pivot point.

13. The suprapubic region compression assembly of claim 11, wherein the first arm is pivotally attached to the upper portion at a first pivot point and the second arm is pivotally attached to the upper portion at a second pivot point spaced from the first pivot point.

14. A method of compressing a suprapubic region of a user to increase a measurable, visible, or usable length of a penis of the user, the method comprising:
   attaching a belt around a waist of the user such that an inner surface of a rigid compression plate secured to the belt engages the suprapubic region of the user, wherein the compression plate comprises a lower portion including a notch and an upper portion, the lower portion having the notch being curved or angled inward relative to the upper portion to compress the suprapubic region of the user;
   positioning the penis of the user adjacent the notch of the compression plate;
   tightening the belt to force the compression plate against the suprapubic region of the user, thereby compressing the suprapubic region to increase the measurable, visible, or usable length of the penis.

15. The method of claim 14, further comprising attaching at least two straps to the compression plate such that the at least two straps urge a lower portion of the compression plate toward the user to compress the suprapubic region of the user.

16. The method of claim 14, further comprising attaching a constriction band to indents of the compression plate such that the constriction band engages and applies pressure to a base of the penis.

17. The method of claim 14, further comprising adjusting a size of the notch by pivoting first and second arms of the compression plate relative to each other.

18. A suprapubic region compression assembly for compressing a suprapubic region of a user, the assembly comprising:
   a compression plate having opposite inner and outer surfaces and opposite left and right side edge margins, the compression plate defining a notch positioned between the left and right side edge margins, the notch configured to receive a penis of the user, wherein the compression plate comprises an upper portion and a lower portion, the lower portion comprising first and second arms pivotally attached to the upper portion, the arms defining the notch such that a size of the notch is adjustable upon movement of the arms relative to each other; and
   a belt configured to urge the compression plate toward the user such that the compression plate engages the suprapubic region of the user to apply pressure to the suprapubic region thereby increasing a measurable, visible, or usable length of the penis.

19. The suprapubic region compression assembly of claim 18, wherein each of the first and second arms is pivotally attached to the upper portion at a pivot point.

20. The suprapubic region compression assembly of claim 18, wherein the first arm is pivotally attached to the upper portion at a first pivot point and the second arm is pivotally attached to the upper portion at a second pivot point spaced from the first pivot point.

* * * * *